Figure 1:
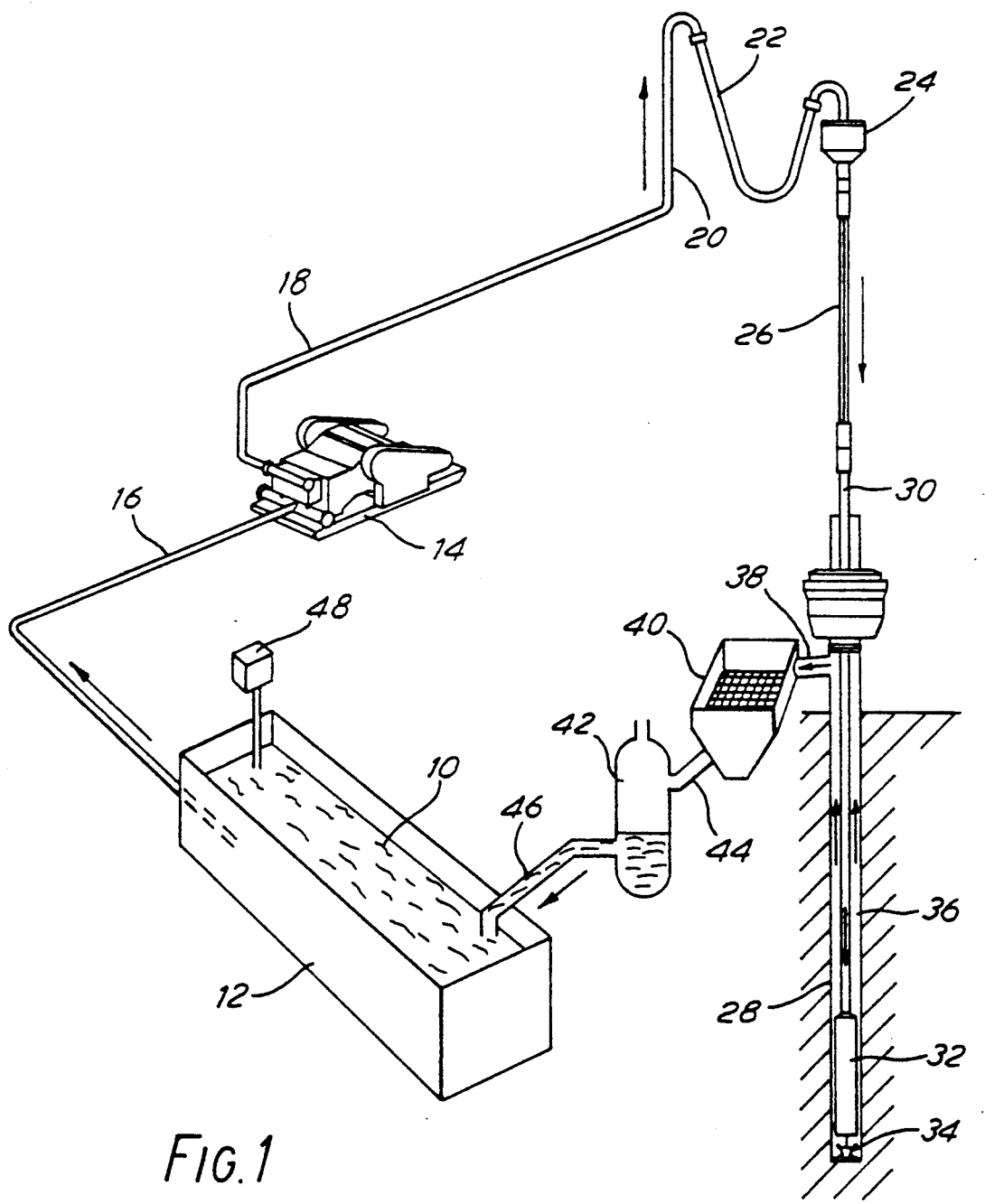

United States Patent [19]
Hughes et al.

[11] Patent Number: 5,161,409
[45] Date of Patent: Nov. 10, 1992

[54] ANALYSIS OF DRILLING SOLIDS SAMPLES

[75] Inventors: Trevor Hughes, Hinton; Timothy Jones, Cottenham, both of England

[73] Assignee: Schlumberger Technology Corporation, Houston, Tex.

[21] Appl. No.: 601,489

[22] Filed: Oct. 22, 1990

[30] Foreign Application Priority Data

Oct. 28, 1989 [GB] United Kingdom ............... 8924346
May 23, 1990 [GB] United Kingdom ............... 9011527
Jul. 5, 1990 [GB] United Kingdom ............... 9014870

[51] Int. Cl.$^5$ .......................... E21B 49/02; G01J 3/00
[52] U.S. Cl. ..................................... 73/153; 250/255; 250/339
[58] Field of Search ............... 73/152, 153, 866, 61.4, 73/61 R; 250/255, 339, 341

[56] References Cited

U.S. PATENT DOCUMENTS

| | | | |
|---|---|---|---|
| 4,149,804 | 4/1979 | Chew, III | 250/255 |
| 4,321,465 | 3/1982 | Stover et al. | |
| 4,608,859 | 9/1986 | Rockley | |
| 4,800,279 | 1/1989 | Hieftje et al. | 250/255 |
| 4,839,516 | 6/1989 | Freeman et al. | |
| 4,852,182 | 7/1989 | Herbin et al. | 73/153 |
| 4,878,382 | 11/1989 | Jones et al. | 73/153 |
| 5,005,406 | 4/1991 | Jasinski et al. | 73/153 |

FOREIGN PATENT DOCUMENTS 0282231 9/1988 European Pat. Off. .
2217838 11/1989 United Kingdom .

OTHER PUBLICATIONS

Brown, James M. et al., "The Quantitative Analysis of Complex, Multi-component Mixtures by FT-IR; The Analysis of Minerals and of Interacting Organic Blends", *Chemical Biological and Industrial Applications of Infrared Spectroscopy*, pp. 111-128, 1985, Great Britain.

Fuller, M. P. et al., "Partial Least-Squares Quantitative Analysis of Infrared Spectroscopic Data. Part II: Application to Detergent Analysis", *Applied Spectroscopy*, vol. 42, No. 2, pp. 228-236, 1988.

*Primary Examiner*—Hezron E. Williams
*Assistant Examiner*—George M. Dombroske
*Attorney, Agent, or Firm*—John J. Ryberg

[57] ABSTRACT

A method of quantitative analysis of solids carrying drilling mud and removed from a drilling fluid circulating in a wellbore being drilled is described. The method comprises the steps of: sampling the removed solids, and analyzing the sample to determine the density of the solids and their weight fraction, drying a known weight of the sample to constant weight so as to obtain the solids in the form of dry solids, and analysis of the latter by an infrared spectroscopy technique. The concentration of the substances in the removed solids is then determined. The method can be applied to the control of the drilling operation by monitoring the quantity of products added to the drilling fluid, such as barite and polymers, or a product coming from the borehole wall or the underground formation being drilled. The invention also applies to the control of the working condition of the mud solids equipment.

16 Claims, 13 Drawing Sheets

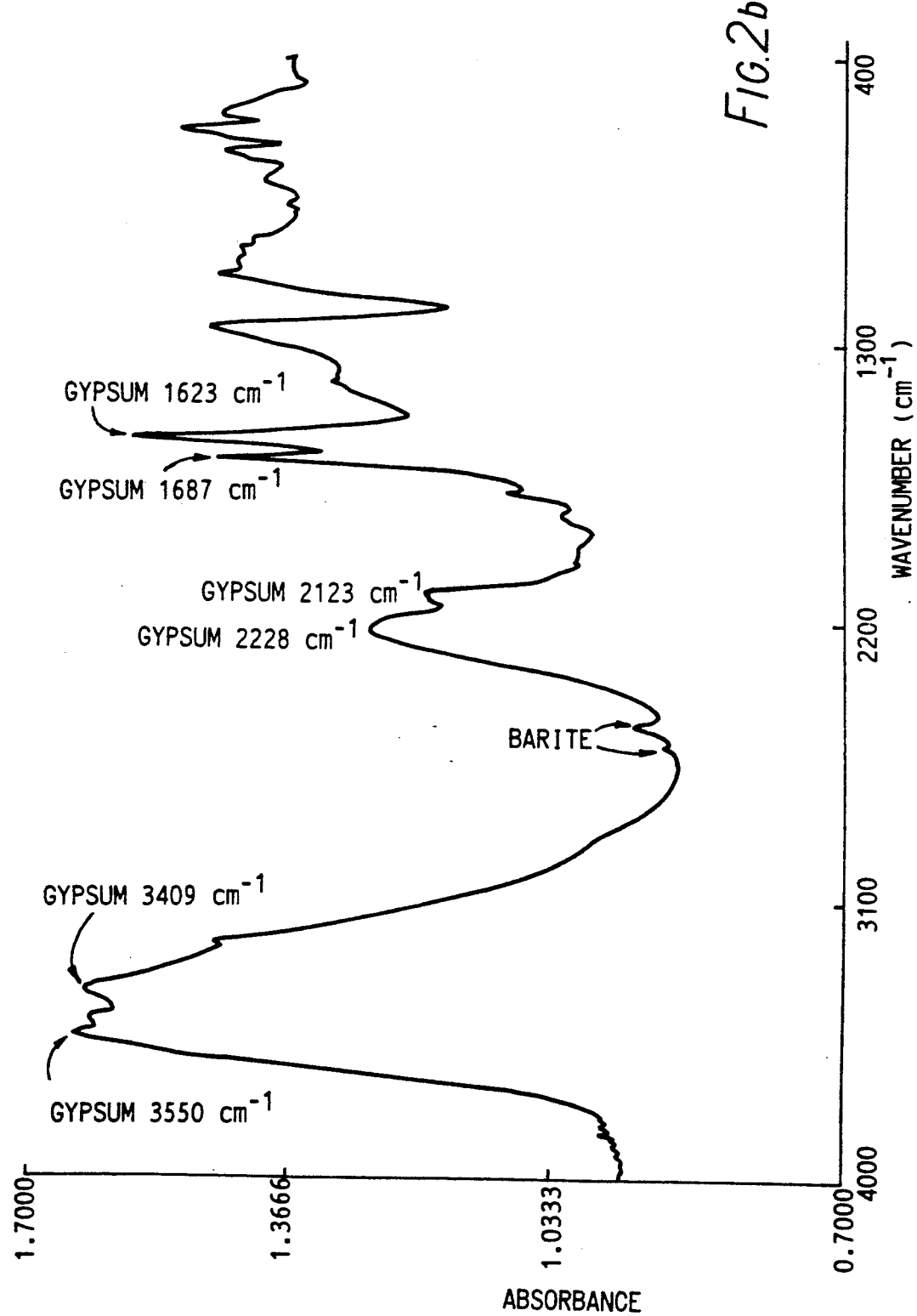

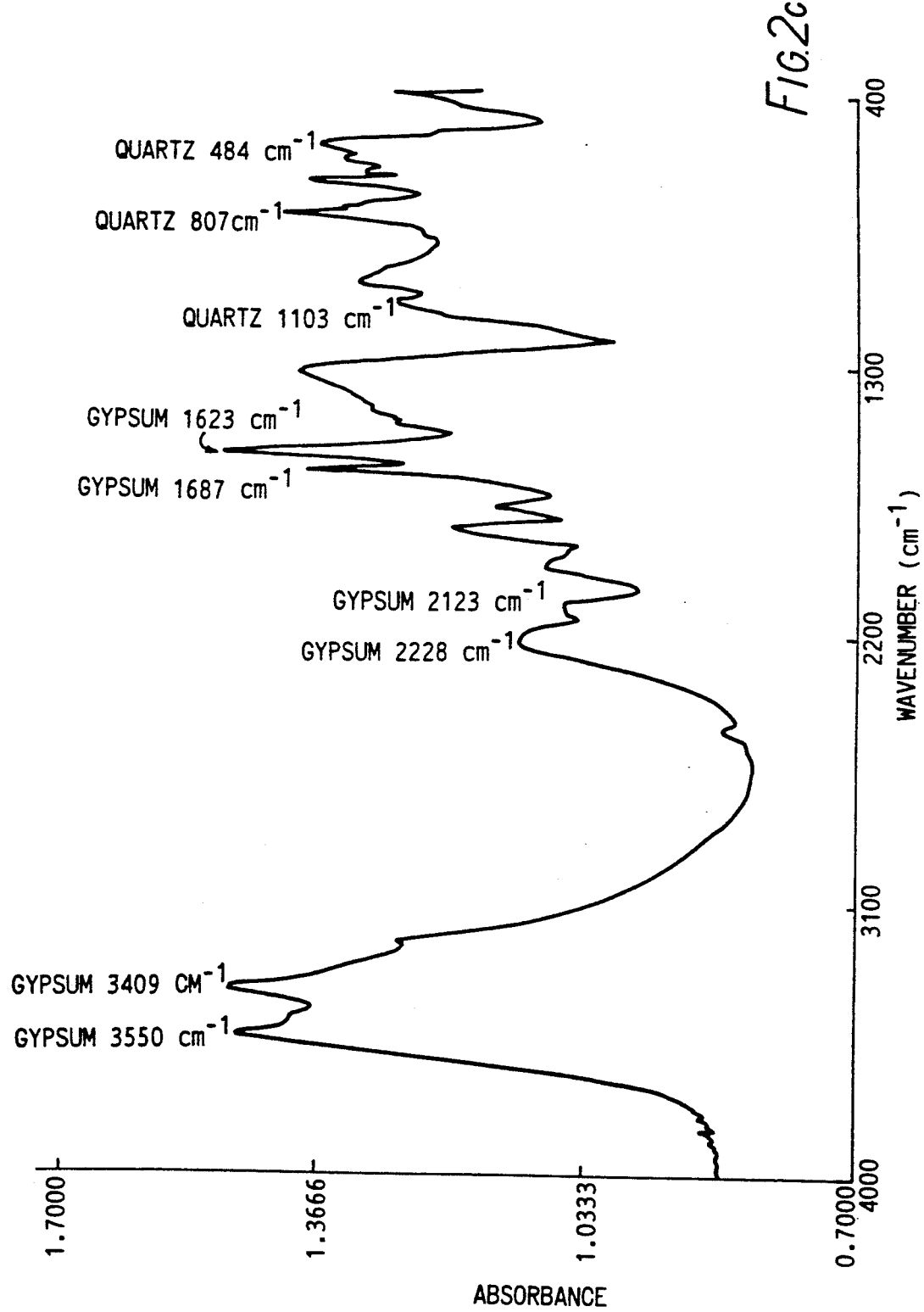

CALIBRATION SAMPLES - BENTONITE

CALIBRATION SAMPLES - CMC-LV

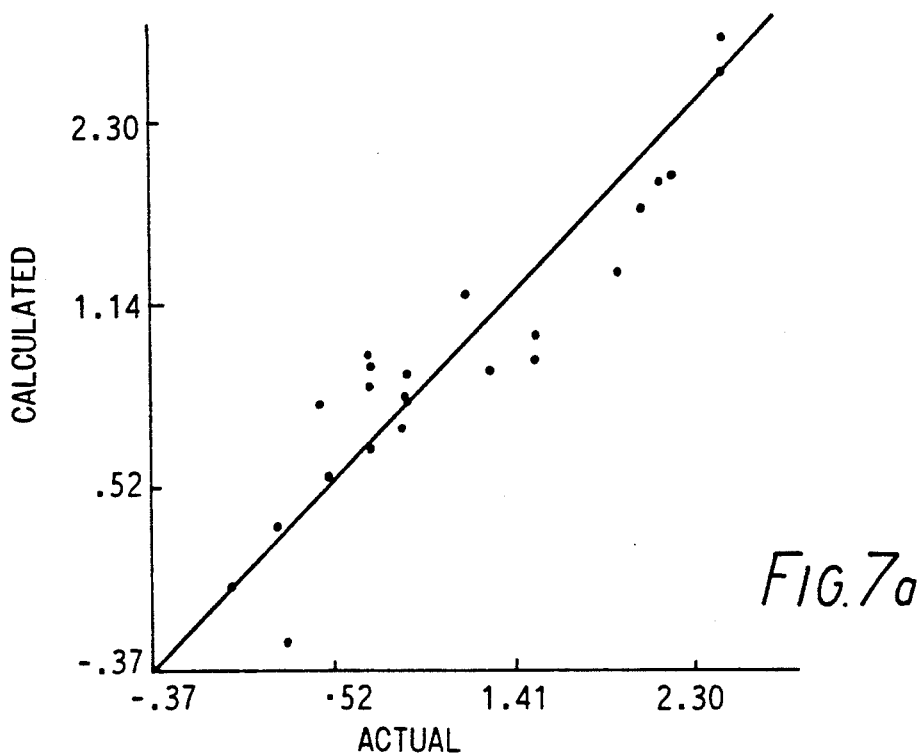

ANALYSIS OF DRILLING SOLIDS SAMPLES

This invention concerns the analysis of drilling solids, and relates in particular to a method of quantitative analysis of the solids in a drilling fluid (usually called "mud") used to drill a well.

In the rotary drilling of wells, such as hydrocarbon wells, a drilling fluid or mud is continuously circulated from the surface down to the bottom of the hole being drilled and back to the surface again. The mud has several functions, one of them being to transport cuttings drilled by the drill bit up to the surface where they are separated from the mud, while another is to impose an hydrostatic pressure on the walls of the bore hole so as to avoid a collapse of the borehole and an influx of gas or liquid from the formations being drilled. The characteristics of the mud are therefore important to monitor and to keep within certain limits. For instance, the viscosity of the mud is an important characteristic since it contributes to the cuttings transport capability of the mud, and clays, such as bentonite clay, are added to the mud so as to keep the drilled cuttings in suspension as they move up the hole (the clay also sheathes the wall of the hole; this thin layer of clay, called filter cake, reduces the loss of mud to permeable formations caused by filtration). The density of the mud is another significant factor. It must be large enough so as to exert a certain hydrostatic pressure on the formation, but not too large to fracture these formations. Weighting materials, barite for example, are added to the mud to make it exert as much pressure as needed to contain the formation pressures. These are examples of the numerous chemicals available to give the mud the exact properties it needs to make it as easy as possible to drill the hole.

Drilling muds are two main types, distinguished by whether water or oil is used as the continuous phase. Water-based muds are typically suspension of bentonite clay, to which further heavier minerals (usually barite), polymers and surfactants are added to optimise the rheology and other physical properties for a particular job. Oil-base drilling fluids, on the other hand, are most commonly water-in-oil emulsions where micron-sized brine droplets, stabilized by emulsifier, are dispersed in a mineral oil, along with organophilic clays, weighting minerals, wetting agents and oil-soluble viscosifiers.

In addition to the products deliberately added in the drilling mud for specific purposes, other materials coming from the formation being drilled and/or from the borehole wall can be present in the mud. These products are mainly in the form of minute particles of solids (an average diameter being about 50–100 microns), and are usually called "fines". Examples of "fines" are silica (quartz), carbonates, and dispersed clay particles. Hereinafter the term "mud products" is used to designate both the mud additives and the "fines".

As noted above, one of the mud's functions is to transport the drilled cuttings up to the surface. The cuttings are then separated off using "solids control" equipment, and the mud, possibly after the addition of one or more materials to restore its make-up and properties, is re-used.

A number of solids control devices are used to remove drilled cuttings and solids from the return mud. The cuttings, which typically have a particle size between several millimeters and about 175 microns, are filtered from the return mud using vibrating screens known as "shale shakers". Sand-sized drilled solids (which have particle sizes in excess of about 75 microns) and slit-sized drilled solids (which have particle sizes in excess of about 2 microns) are removed by hydrocyclone desanders and hydrocyclone desilters respectively. Under certain circumstances, decanting centrifuges may also be used to remove fine drilled solids which have particle sizes less than 20 microns. A typical set-up for a solids control system is seen in FIG. 1 of the accompanying Drawings, which shows the main components of the mud circulation equipment. The mud (10) is contained in a mud pit (12), called the active tank. A pump (14) draws up the mud from the pit through a pipe (16), and forces the mud through the discharge line (18), the stand pipe (20), the rotary hose (22) and the swivel (24). The mud then flows into the kelly (26) and down the borehole (28) in the drill pipe (30) and the drill collars (32). The mud reaches the bottom of the hole at the drill bit (34), and then flows up to the surface in the annulus (36) and in the mud return line (38). The return mud, laden with drilled material, then falls over a vibrating screen-like device (40), called a shale shaker. Shale shaker underflow mud is fed (via line 44) to additional solids control equipment (42), which may include a combination of devices such as a degasser, hydrocyclone desander/desilter, and/or decanting centrifuges. Solids control equipment underflow mud is fed (via line 46) to the active tank 12. Batches of freshly prepared mud and quantities of mud products are added to the active tank and mud 10 during drilling. The batches of freshly prepared mud replaced (i) volumes of mud taken up by an increasing volume of borehole 28, (ii) volumes of mud lost on solids removal by the solids control equipment 40 and 42, and (iii) volumes of mud which may be discharged due to a loss of desired properties (such as mud containing large quantities of fine drilled solids which cannot be removed by the solids control equipment but which would slow down drilling if recirculated into the borehole). Quantities of mud products are added to mud in the active tank so as to maintain their concentration specified in the original mud formulation.

It will be readily apparent that for a correct understanding of the drilling progress it is necessary to have results from accurate analysis not only of the mud but also of the solids separated therefrom by the various stages of the solids control equipment. So far as the latter are concerned, it should be borne in mind that, whilst the composition of the removed drilled cuttings and solids is typically dominated by mineral components originating from the rock formations being drilled, there will also be present considerable quantities of added mud product components coming from the mud formation.

To give some idea of the scale of the problem it should be noted that typical field data indicates that approximately one liter of mud may be removed by the solids control equipment for every one liter of formation drilled. Therefore, in order to maintain a constant volume of mud is surface holding tanks, the mud engineer needs in principle to add two liters of fresh mud volume for every one liter of formation drilled (in practice, additional volumes of fresh mud may be added to replace return mud which is discarded due to its non-optimum properties). Current mud engineering practices do not attempt to evaluate and account for losses of mud products in solids removed by the solids control equipment or in discarded mud.

Investigations have also indicated that for every volume of dried cuttings produced by a typical shale shaker configuration an equal volume of mud is removed. Such a degree of "contamination" of cuttings by a typical barite-weighted mud formulation (with mud density, $\rho_{(m)}=1.2$ kg/l and average mud solids density, $\rho_{(ms)}=4.1$ kg/l) used to drill a typical formation (with average formation density, $\rho_{(f)}=2.6$ kg/l) produces dried cuttings solids which contain 89.8 weight percent formation mineral components and 10.2 weight percent mud product components. And it is well known that considerable quantities of the coarser fractions of API-grade barite are present in solids removed by the hydrocyclones.

A variety of techniques are employed to determine the nature and amounts of the numerous components in the mud and the removed solids, but not all are equally satisfactory. Thus: the current field technique used to determine the solids content of a mud sample involves the use of a retort to dry the sample to constant weight. This technique measures percentage solids by volume and by weight, allowing an average solids density to be calculated; the latter data is used to calculate a percentage "high gravity solids" (assuming a high gravity solids density, $\rho_{(hgs)}=4.3$ kg/l) and a percentage of "low gravity solids" (assuming a low gravity solids density $\rho_{(lgs)}=2.5$ kg/l). Such a technique may also be applied to an analysis of solids removed by the solids control equipment, but here it can be highly inaccurate; for example, an apparently increasing high gravity fraction in solids removed by a hydrocyclone may in fact be caused by an increasing average formation density due a change of drilled lithology. Further inaccuracies may be introduced as a result of varying concentrations of salt components originating from added mud products or, more particularly, when drilling through evaporite sequences.

The published and presently used methods for the analysis of drilled cuttings have focussed on a qualitative and/or quantitative assessment of mineral components in order to evaluate the composition of drilled lithologies. During a conventional mud logging operation, cuttings samples may be taken from the shale shaker after drilling intervals of 20-50 feet. Each cuttings sample is evaluated by a geologist who carries out a number of quantitative tests and provides a lithological description for the mud log. The technique most widely used in the industry for a quantitative determination of the mineral components in drilled cuttings and core samples is x-ray diffraction analysis (XRD). XRD is normally capable of quantifying minerals within a relative accuracy of ±5-10%, however, crystallinity differences between standards and unknown samples, and the presence of amorphous material (for example, organic material such as kerogen from the formation, or contaminant polymeric mud products), may introduce considerable systematic error.

Another method proposed for the quantitative analysis of mineral components in core samples and drilled cuttings (and in core samples) is the subject of two recent U.S. patents (U.S. Pat. Nos. 4,608,859 and 4,839,516), namely infrared spectroscopy (particularly Fourier-transform infrared spectroscopy, FTIR) in the wave number range 5,000 to 400 cm$^{-1}$ (2,000 to 25,000 nanometers), corresponding to mid-range infrared. The method described in the latter patent involves: (i) a cleaning procedure to remove components other than the analyte mineral components; (ii) the reduction of sample particle size to an average of one micron, with no particles larger than two microns; (iii) the dilution of the crushed sample with potassium bromide (KBr); (iv) the production of a pressed disc from which a transmission FTIR spectrum is obtained; and (v) a comparison of the sample spectrum with transmission spectra for pure minerals in order to obtain a quantitative mineraological analysis. It is important to note that the method described states that any hydrocarbon in the core sample is removed by techniques such as toluene solvent extraction or $CO_2$ cleaning prior to the mineralogical analysis; the Patent does not describe a method to determine the hydrocarbon content or the content of any component other than the mineral components in a core or cuttings sample.

The use of FTIR spectroscopy to determine mineral composition of rock samples, such as shale samples, has also been described in the article entitled *The quantitative analysis of complex multicomponent mixtures by FT-IR; the analysis of minerals and of interacting blends* by James M. Brown and James J. Elliott, published in the book *Chemical, Biological and Industrial Applications of Infrared Spectroscopy*, a Wiley-Interscience publication, 1985. The article proposes a method for the determination of minerals in rock samples which involves: (i) pregrinding the mineral to 325 mesh; (ii) dispersion of the ground mineral in KBr; (iii) the production of a pressed disc from which a transmission FTIR spectrum is obtained; and (iv) a comparison of the sample spectrum with transmission spectra for pure minerals in order to obtain a quantitative mineralogical analysis.

It is important to note that the above mentioned U.S. patents and the Brown and Elliott article propose methods for the quantitative analysis of mineral components in cleaned drilled cuttings, and in core and rock samples; there is no suggestion that the method might be of value for the quantitative analysis of mud products in drilled cuttings samples.

An alternative infrared analytical technique is the subject of GB Patent Specification No: 2,217,838 which is mainly concerned with the specific determination of oils and other materials, for which it can be advantageous to use the overtone and combination bands of the fundamental O—H, C—H and N—H stretching vibrations since they are generally more sensitive to chemical composition than the fundamental bands. However, the overtone and combination bands of the fundamental vibration frequencies of bands containing heavier atoms, commonly found in minerals (e.g. S—O, Si—O) and polymers (e.g. C—N, C—O) are found in the mid-infrared and therefore are not revealed. By opposition, these heavier materials are particularly well revealed by the diffuse reflectance technique described herein.

It will be evident that accurate evaluation of mud products in solids removed by the solids control equipment, together with a corresponding evaluation for mud entering and exiting the equipment, provides information with which to compile a mass balance for the mud components on a regular basis. Such information may be used to account for the mud products during a mud engineering service. Regular mass balances for each mud product provide useful information with which both to evaluate and account for their losses in solids removed by the solids control equipment and to monitor the performance of mud products such as an encapsulating polymer. However, none of the analytical techniques presently in use allow this to be effected, for none accurately analyse the removed solids because they either ignore or incorrectly assess the mud products carried by these removed solids. The "contamination" of the cuttings by barite has already been alluded to, but there are a number of other possibilities that give rise to particular concern. Thus, this type of problem may be aggravated by the very nature of the mud products. For instance, certain polymeric mud products— e.g. partially hydrolysed polyacrylamide (PHPA)—are specifically added to the mud formulation in order to stabilise cuttings generated by particularly water-sensitive formations such as shales; they adsorb on and encapsulate water-sensitive cuttings, allowing the drilled material to be more efficiently removed by the solids control equipment. At present, there are no adequate analytical techniques to monitor the concentration of such polymeric products in removed solids.

In addition, a major area of environmental concern is the retention of oil on drilled cuttings either when using an oil-based mud formation or when lubricant oils are added to a water-based mud formulation. At present, there are no adequate analytical techniques to determine the oil content of solids removed by the solids control equipment, but one is required in order to provide the necessary information for an accurate accounting for the base or lubricant oil (and to enable an assessment of the efficiency of the processes used to recover the oil from solids removed by the solids control equipment).

In our co-pending GB Application No. 9011527 there is described a quantitative analysis method for mud products, which method uses mid-range infrared spectroscopy, most preferably Fourier-transform infrared spectroscopy carried out in reflectance mode on a raw, undiluted sample of dried and powdered mud solids. It has now rather surprisingly been found that essentially the same technique may be applied to the removed mud solids—that is to say, to the drilled cuttings and other removed solid materials together with any mud products carried thereby—to provide an efficient quantitative analysis of the removed solids with respect to the nature and content both of the formation-derived materials and of the mud-derived materials. The invention proposes, therefore, that some or all of the solids removed from a drilling mud be both qualitatively and quantitatively determined by the mid-range IR spectroscopic analysis of a sample thereof, this method involving: preparing the sample in dry powder form; analysing the powder in an IR spectrometer, to obtain an IR spectrum; and determining therefrom a value characteristic of the concentration in the sample of one or more of its constituents. It will be seen, then, that one object of the invention is to provide a method of determining the concentration of mud product components and mineral components in the solids samples. A further object is to enable the use of the thus-measured concentrations in conjunction with corresponding data for certain mud streams (as described in our aforementioned copending Application) so as to assess:

the accountability of mud products used to prepare a specified mud formation, and of mud products used to maintain the said mud formulation during drilling;

the efficiency of drilled cuttings/solids removal by solids control equipment;

the efficiency of certain mud products (such as encapsulating polymers) which may be specifically added to the mud formation in order to improve the removal of certain drilled solids (such as water-sensitive shales);

the stability of a drilled hole interval as indicated by an assessment of its gauge; and the mixing properties of certain surface mud holding tanks (such as the active tank).

Evaluation procedures required in order to carry out the above assessments through a compilation of several mass balances are described in detail hereinafter.

Accordingly, the invention provides a method of quantitative analysis of drilled cuttings/solids samples obtained in the course of the drilling of a borehole using a "mud" drilling fluid, in which method the solids removed by one or more of the solids control devices are representatively sampled and the sample is analysed, the method comprising the following steps:

the sample is homogenised;

a known weight of the homogenised sample is dried to constant weight, and the weight fraction of solids, $W_{(s)}$ in the sample is determined;

the dried solids are crushed and homogenised to form a powder suitable for quantitative infrared analysis, and the powder is analysed in a mid-range infrared spectrometer in order to obtain an infrared spectrum; and knowing the solids weight fraction, a value representative of the quantity of at least one of the mud product components and/or at least one of the mineral components in the sample is determined from the spectrum.

Where the selected component was originally in a liquid state, a preliminary determination of the homogenised sample's density, $\rho_{(s)}$, allows the subsequent determination from the spectrum of that component's concentration.

The material being analysed according to the method of the invention is a combination of the solids removed from the mud—that is, the cuttings, etc—and the solids retained in the mud—thus, the mud products—and carried by the removed solids. The technique of analysis of the invention involves no separation process of these substances, and allows the quantitative analysis of them all—thus, including products such as polymer(s) present in the drilling fluid. The proposed method also has the advantage of determining the quantities of the components by one analysis only: the polymer(s) and the other mud products such as added mud solids (e.g. barite, bentonite) and "fines" (e.g. carbonates, quartz) can be quantified simultaneously with the minerals etc. in the removed cuttings. The mud product components are mainly polymer(s), bentonite clay and barite, and possibly oil. The various mineral components include quartz, feldspars, clay minerals (such as monotomorillonite, illite and kaolinite, which can be detected individually), carbonates (such as dolomite and calcite) and sulphates (such as gypsum and anhydrite).

The invention used mid-range infrared spectroscopy—that is, spectroscopy employing infrared generally in the middle of the range of wavelengths recognised as infrared. For the purpose of this invention mid-range infrared is generally defined as infrared being a wavelength in the range 2,500 to 25,000 nanometers (a wave number range of from 4,000 to 400 cm$^{-1}$). By contrast, near-range infrared is generally from 800 to 3,000 nanometers, while far-range infrared is generally beyond 25,000 nanometers and up to the microwave region.

The spectrum is preferably obtained by Fourier transform infrared (FTIR) spectroscopy, and by a diffuse reflectance technique.

The principles of IR spectroscope are well known, and in general the technique requires the sample being analysed to be "mounted" on or within an IR-transparent carrier. Thus, for example, in conventional transmission spectroscopy the sample may be pasted with NUJOL (or some similar paste) and supported between two rocksalt (sodium chloride) plates, or it is incorporated into a salt powder, and pressed into a small lozenge, or pellet. In this latter technique the preparation of the powder for infrared analysis includes the mixing of a known weight of dried drilling fluid solids with a halide salt to form a mixture, grinding the mixture until the particle size of the solids is no more 2 microns to obtain the desired powder, and then pressing the powder into a pellet. The halide salt is preferably potassium bromide or sodium chloride. In conventional reflectance spectrosocpy, which technique is usable with advantage in the method of this invention, the sample is simply incorporated in a salt powder (but not, of course, pelleted).

The diffuse reflectance technique is particularly preferred for the present invention for the following reasons:

It is a more rapid technique, and avoids the manufacture of halide pellets.

Overtone and weaker bands in the infrared spectrum are often more prominent in diffuse reflectance than in direct transmission mode; such bands may be essential for quantification of the lower concentrations of mud products (such as polymers) and mineral components (such as accessory minerals) in solids samples.

Direct transmission techniques give rise to intense absorption bands in the infrared spectrum which may not be suitable for use in linear quantitative techniques.

Larger sub-sample weights are used in the diffuse reflection technique—typically a 0.4 g sub-sample representing the primary sample may be used for an evaluation of solids removed by a solids control device. In comparison, a typical 0.004 g sub-sample as used in direct transmission techniques may not adequately represent the primary sample composition. Also, the analytical problems of obtaining an accurate sub-sample weight are reduced by using a diffuse reflectance technique.

The last two mentioned reasons may prevent a transmission technique from being used to evaluate mud products and minerals in solids removed by the solids control equipment. They may also, however, required a significant modification in the reflectance method itself, for while a reflectance spectrum obtained from a salt/sample powder admixture can be perfectly satisfactory, in a reflectance method of this type a high proportion of the returned IR energy has in fact undergone transmission through the surface "layers" of the sample powder, and recent work has shown that, because of the relatively similar refractive indices of the materials involved, one result of effectively incorporating the sample solids within the salt is for refractive effects to mask the weaker signals produced by some of the less plentiful sample components. It has now been found that a rather different—and in some ways markedly superior—spectrum can very usefully be obtained by analysing the sample powder "raw" (as it were) rather than incorporated with a halide salt. Such a modification of the basic techniques has been described (with Test Results) in our aforementioned GB Application No: 9011527, where it has been shown to be of considerable value, and may with advantage also be used in connection with the present invention.

Whether the spectroscopy is carried out by transmission or by reflectance, and if the latter whether with the sample incorporated with a halide salt or not, the interpretation of the concentration of the products is preferably achieved by first obtaining the infrared spectra of known multi-component compositions of the drilling solids, and by generating a calibration model from those spectra.

The technique of analysis of the invention involves no separation process (e.g. filtration and/or centrifugation) of the mud product components or the mineral components from the drilled cuttings/solids sample. More precisely, the invention relates to a method of quantitative analysis of "whole" drilled cuttings/solids samples which contain mud products, drilled minerals, dissolved salts and base fluid. The proposed method has the advantage that mud product and mineral components are determined simultaneously (by one analysis only). In order to ascertain whether erosion of the open wellbore has occurred a quantitative mineralogical analysis of the "whole" drilled cuttings sample may be compared to a corresponding analysis of its "cavings" fraction.

Figure 2A:
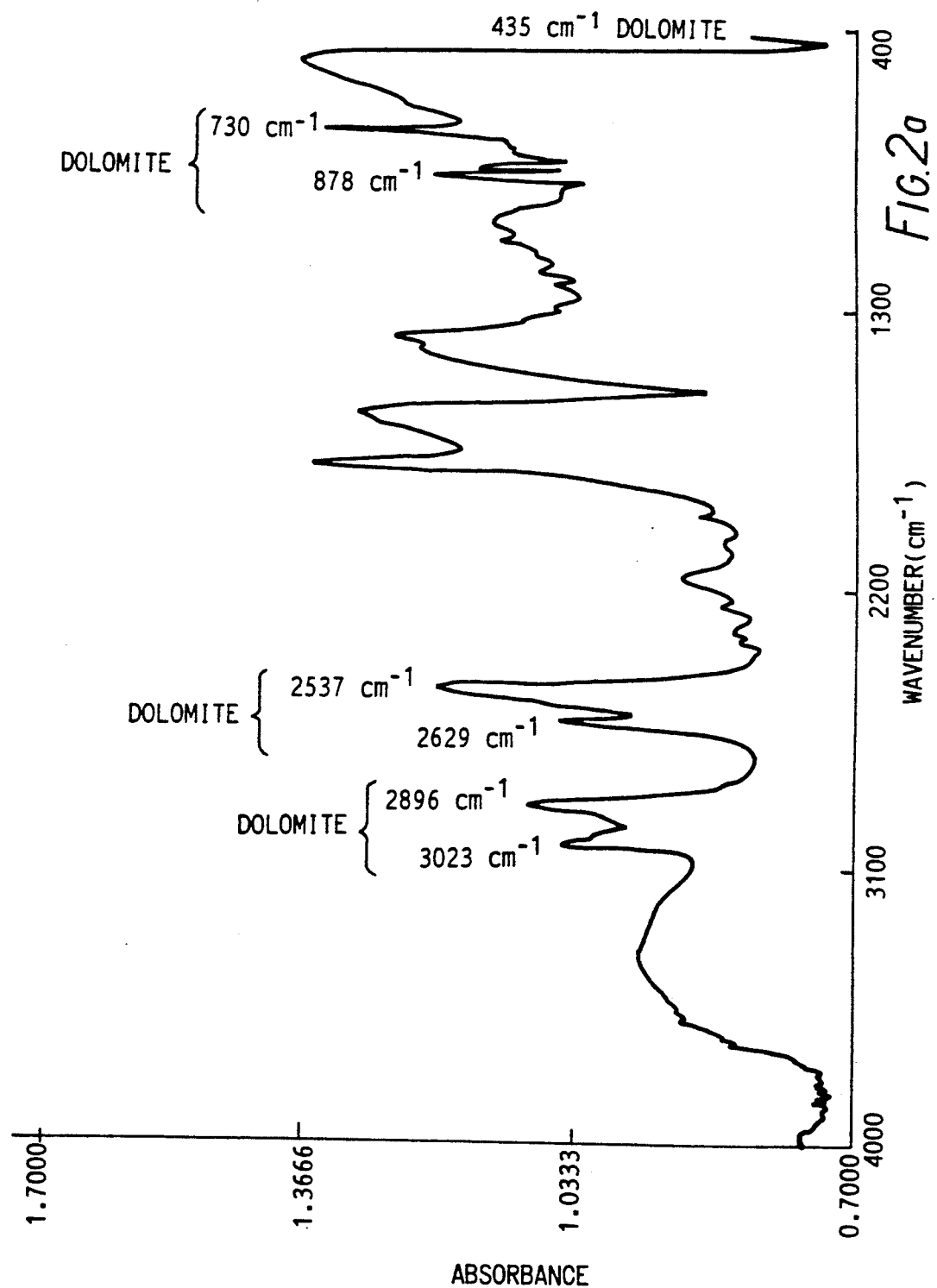
Figure 3A:
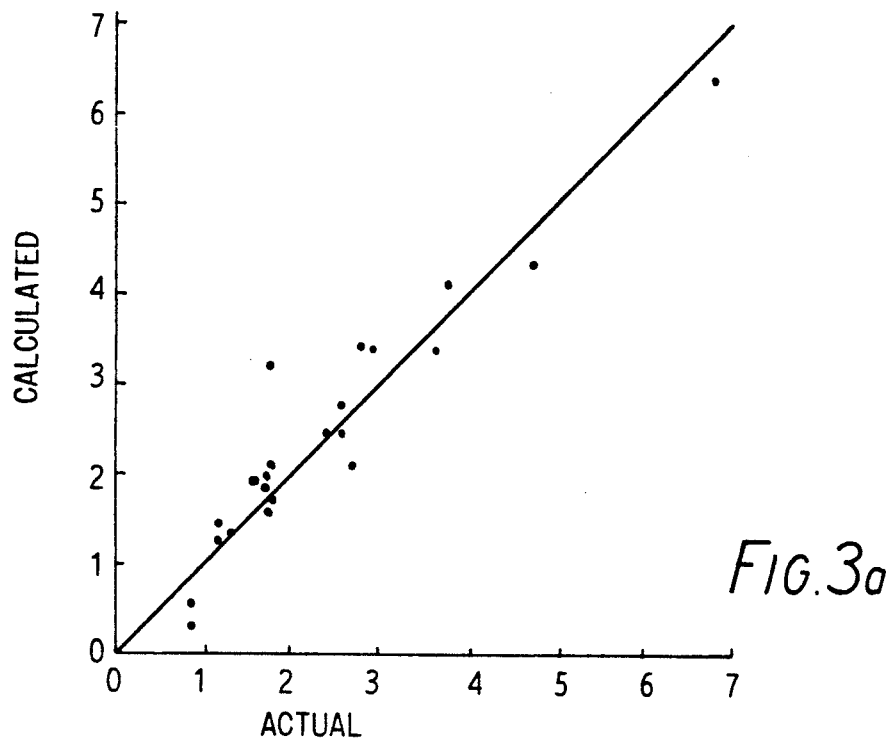
Figure 3B:
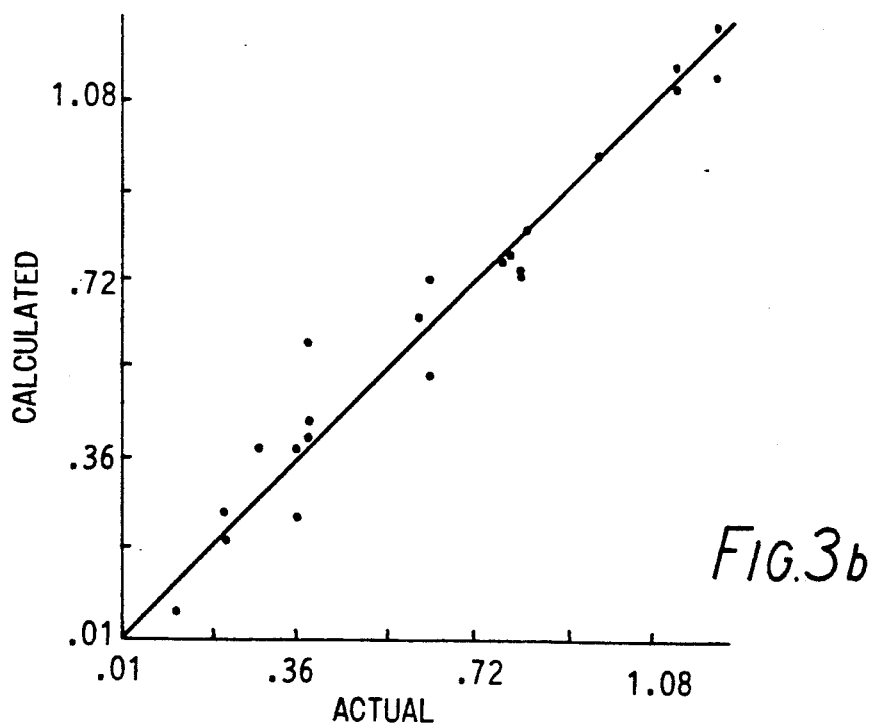
Figure 3C:
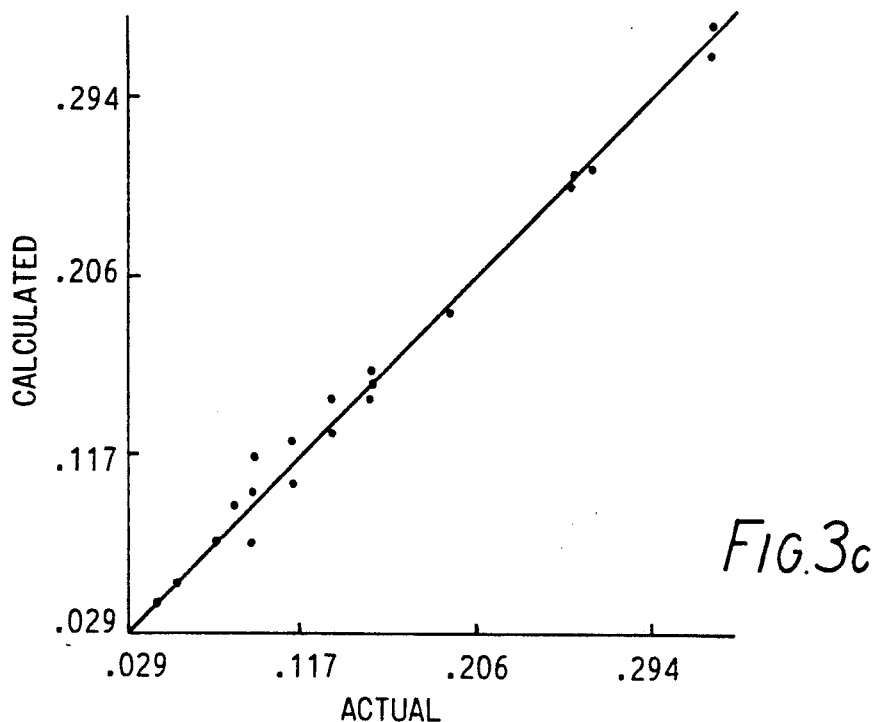
Figure 3D:
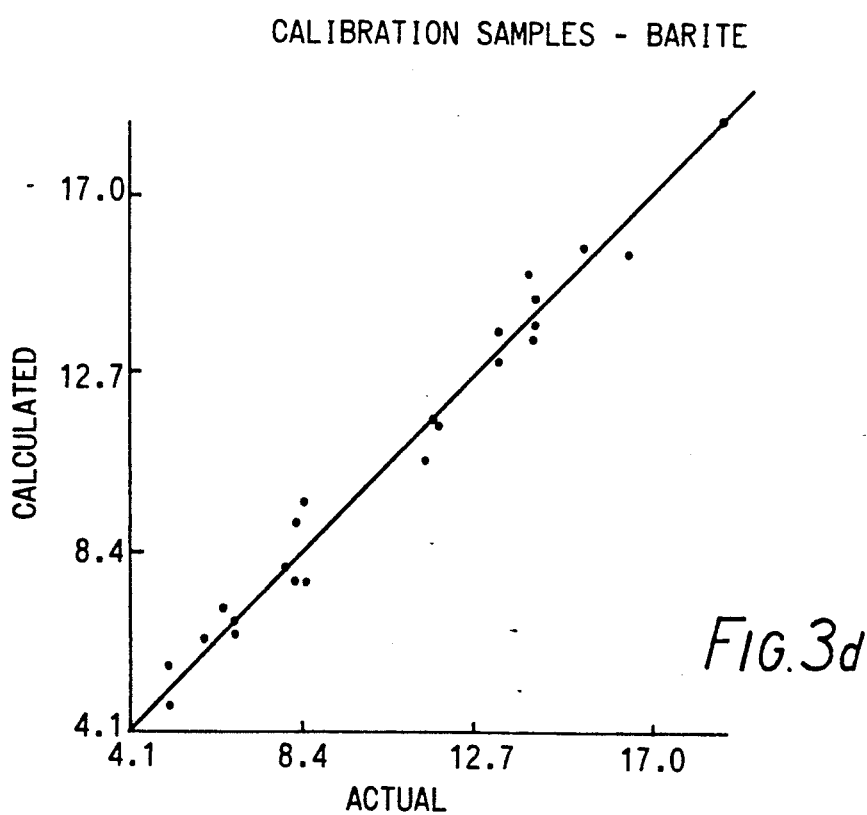
Figure 4A:
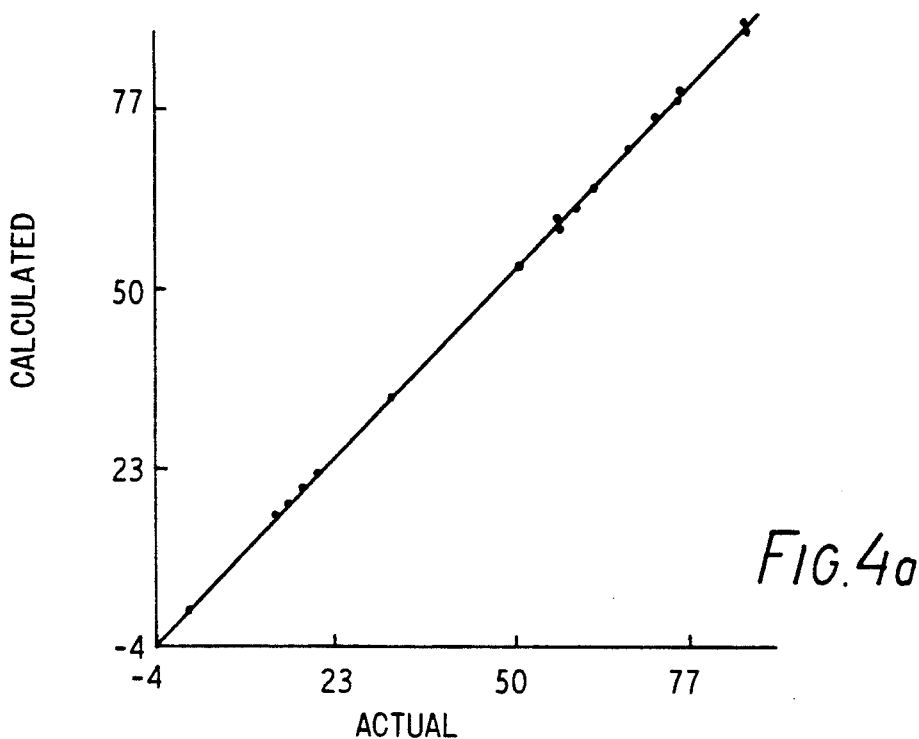
Figure 4B:
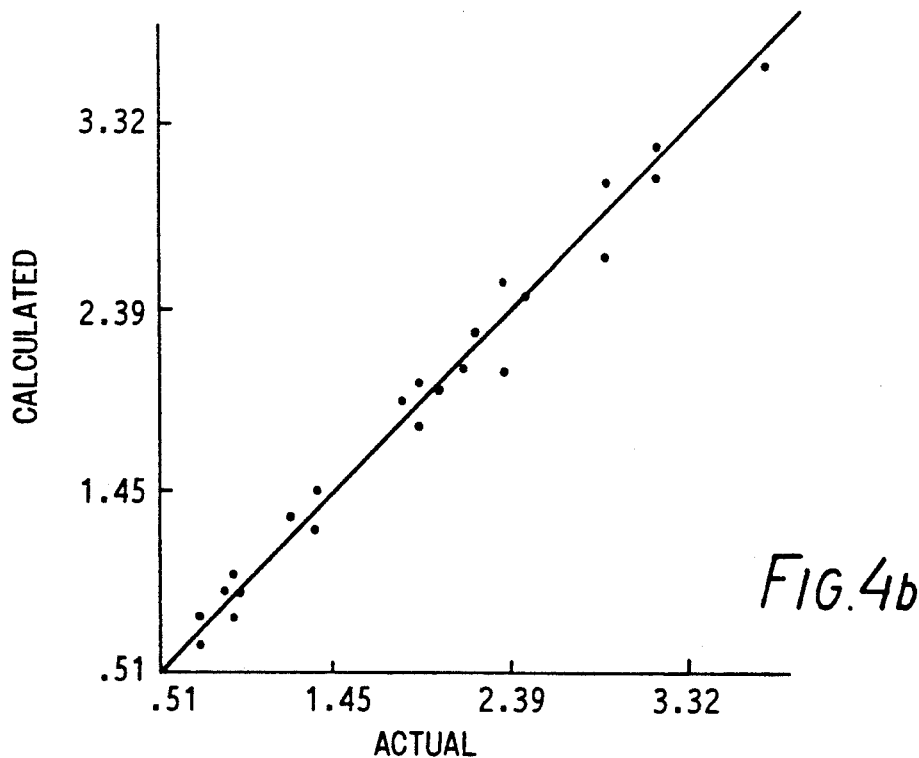
Figure 4C:
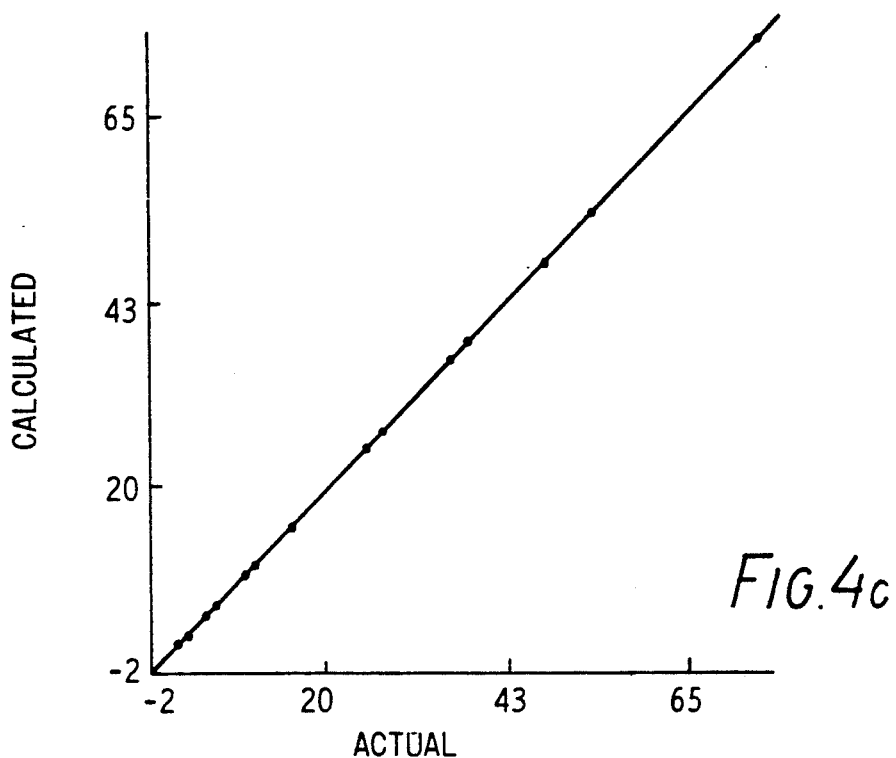
Figure 4D:
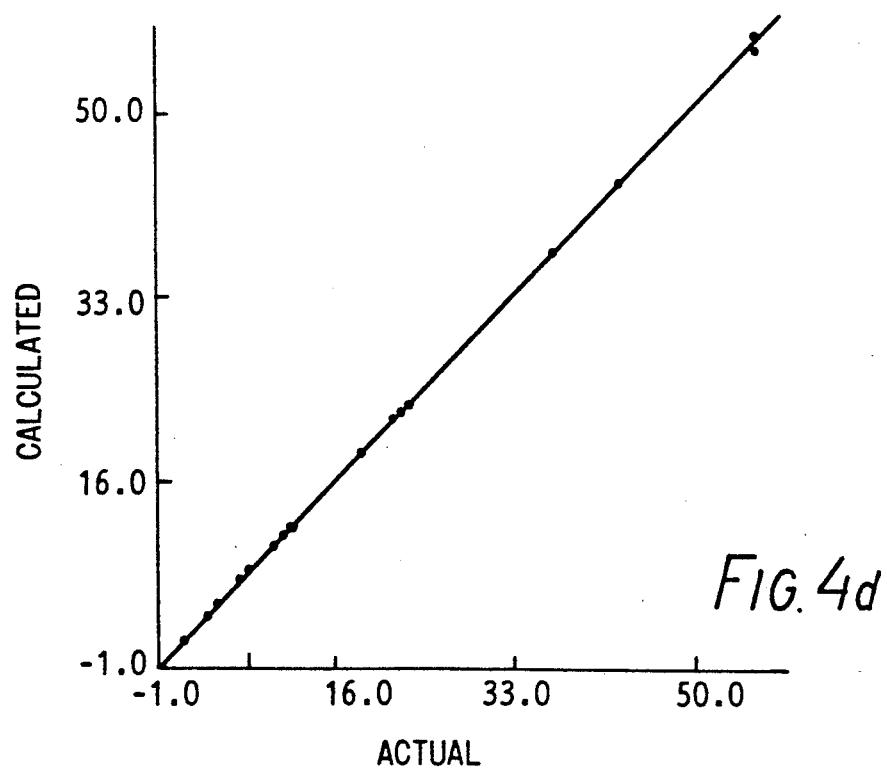
Figure 5:
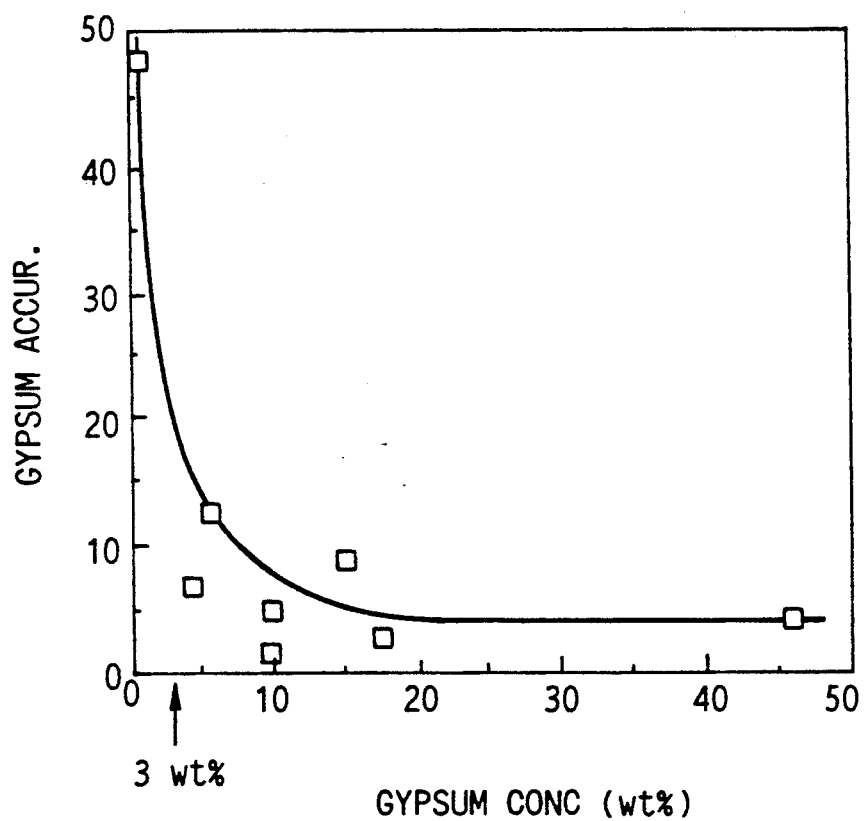

Various aspects of the invention are now described, in more detail, though by way of illustration only, and with reference to the accompanying Examples and Drawings, in which latter FIG. 1 shows a schematic layout of the mud solids removal equipment;

FIG. 2A-C show FTIR spectra for various minerals and mineral combinations;

FIGS. 3A-D show mud product calibration curves;

FIGS. 4A-D show mineral calibration curves;

FIG. 5 shows the correlation between results accuracy and gypsum concentration;

FIGS. 6A-D show further mud product calibration curves; and

Figure 7C:
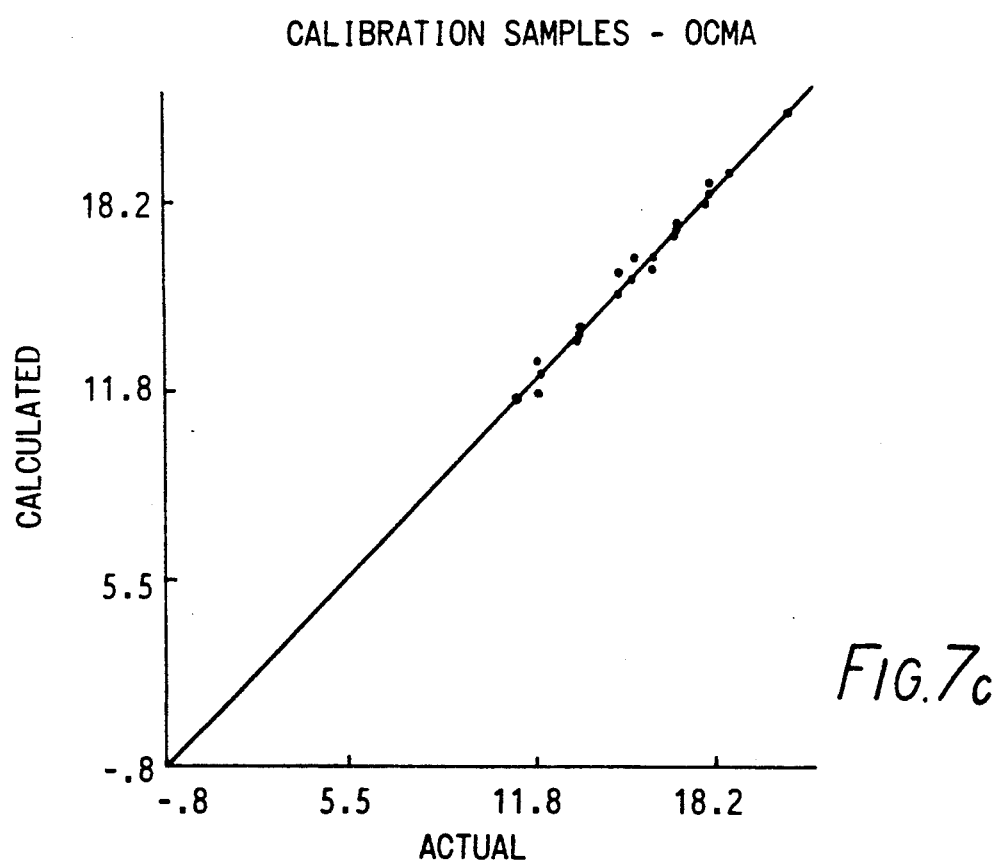

FIGS. 7A-C show further mineral calibration curves.

PROCEDURES FOR MASS BALANCING; SAMPLING AND MATHEMATICAL CONSIDERATIONS

Mass Balancing Mathematics

An evaluation of mud product and mineral components in drilled cuttings/solids and various mud streams flowing through the mud circulation equipment may be used to compile a number of mass balances each of which is designed to assess various aspects of mud engineering service during drilling. Five such mass balances have been identified in Table 1; each mass balance requires an evaluation of one or more mud products and/or mineral components in the indicated input and output streams. As an examples, detailed procedures and considerations for a compilation of mass balance A are described below.

The input mass of return mud dumped onto a shale shaker per unit time is equal to the output mass of drilled cuttings plus the mass of shaker underflow mud generated per unit time. The unit of time across which a representative mass balance may be compiled will depend on working conditions during drilling.

During drilling, the mass of drilled material generated per unit time, A, will depend on the rate of penetration (ROP), the hole diameter (hd) and the average formation density ($\bar{\rho}_{(f)}$):

$$A = \Pi \left(\frac{hd}{2}\right)^2 \times ROP \times \rho_{(f)} \quad (1)$$

The weight fraction of drilled material in return mud loaded onto the shale shaker, B, will depend on A, the return mud flow rate, $Q_{(rm)}$ and the return mud density, $\rho_{(rm)}$:

$$B = \frac{[A]}{Q_{(rm)} \times \rho_{(rm)}} \quad (2)$$

For the typical example wherein:
ROP = 0.00254 m/s (30 ft/hr);
hd = 0.31115 m (12½ inches);
$\rho_{(f)}$ = 2600 kg/m³ (2.6 kg/l);
$Q_{(rm)}$ = 0.020 m³/s (20 l/s); and
$\rho_{(rm)}$ = 1200 kg/m³ (1.2 kg/l)
a substitution of these values gives:
A = 0.502 kg/s; and
B = 0.0209.

For such a typical example, a representative shale shaker mass balance may be obtained by evaluating input and output material over a five minute period. Five minutes of drilling depends the wellbore by 0.762 m and generates 150.48 kg of drilled material which is carried to the surface in 0.6 m³ (7200 kg) of return mud. Assuming that the shale shaker removes (i) 60 wt. % of the drilled material and (ii) one liter of mud per one liter of formation drilled, then the 7200 kg batch of input return mud will generate 159.74 kg of output "wet" drilled cuttings (containing 90.29 kg drilled material and 69.46 kg return mud) and 7040.26 kg of output shaker underflow mud.

SAMPLING

In order to achieve the mud engineering objective(s) for the shale shaker mass balance (refer to Table 1), it is necessary to evaluate the composition of input and output streams. The accuracy of such an evaluation depends on:

Representative primary sampling of input and output streams.

Representative secondary sampling of primary samples in order to obtain suitable sub-samples for analysis.

Accurate quantification of mud product and/or mineral component(s) in subsamples.

Representative primary samples of the input return mud stream and output shaker underflow stream may be conveniently obtained by taking a one liter sample from well mixed "averaging" tanks (as proposed in the patent specification of British Patent Application No: 8926778.5). For example, a one liter primary sample of return mud taken from a well mixed averaging tank containing a 0.6 m³ mud volume in steady state represents 0.6 m³ of input return mud.

Representative primary samples of drilled cuttings generated from the 0.6 m³ input batch of return mud may be conveniently sampled by a device such as a mechanical sample receiver which collects "oversize" material falling off 5% of the shaker screen width; the sample receiver moves across the full width of the shaker at an optimum frequency during the sampling period in order to ensure that the primary sample collected represents the entire output stream. Such a mechanical sample receiver will take a 5% cut of the entire output stream—i.e. a 0.0046 m³ (7.96 kg) primary sample is taken from the total of 0.0926 m³ (159.46 kg) of "wet" drilled cuttings material generated from the 0.6 m³ (7200 kg) input batch of return mud. The pre-tared sample receiver is reweighed after collection of the primary sample; the primary sample weight, $M_{(ps)}$ is used to calculate the weight of the entire output stream, C using the following relationship:

$$C = M/0.05 \quad (3)$$

The primary sample is thoroughly homogenised using a high speed blender prior to taking a secondary sample for subsequent analysis. In practice, it may be necessary to add a known weight of deionised water to the primary sample in order to achieve thorough homogenisation. The secondary sample is analysed as follows:

A known sample volume is weighed in order to determine sample density; a known sample weight is then dried to constant weight in order to determine the weight fraction of solids, $W_{(s)}$; due corrections for the known weight of deionised water added in order to homogenise the primary sample and the weight of residual salts in the dried solids residue are taken into account. Procedures for the determination of mud product and/or mineral component(s) in the dried solids samples are given hereinbefore.

A typical shale shaker mass balance is shown in Table 2. Such a mass balance may be complied on a regular basis so as to assess drilled solids removal efficiency and to account for losses of mud products during a mud engineering service. The efficiency of solids removal by the shale shaker(s) and other solids control devices depends on the particle size distribution of drilled solids contained in the return mud; regular mass balancing may be used to optimise drilled solids removal efficiency according to drilled lithology. Field data has indicated that approximately one liter of return mud is removed by a shale shaker per one liter of formation drilled; the mass balance given in Table 2 assumes such a mud removal, and further indicates that, when using a typical weighted mud formulation, 20 kg of barite is removed per m³ of return mud loaded onto the shale shaker (at this rate, over a 24 hour period nearly six metric tons of barite would be removed).

Experimental data obtained from an evaluation of drilled cuttings/solids generated from two different formations using two different mud formulations are given hereinafter.

SPECTROSCOPIC TECHNIQUES

The dried mud solids and polymers are prepared for quantification using infrared spectroscopy. Firstly, there is taken an accurate weight of dried mud solids and polymers. This may be used as it is or it may be mixed with a halide salt (such as potassium bromide or sodium chloride), the chosen concentration of mud solids being about 5 wight percent (the halide salt decreases the difference of refractive indexes between the air and the mixture, and therefore decreases the loss of infrared radiation by reflection on the solids, but the dilution may result in trace components becoming undetectable). The whole is ground in a ball mill or pestle and mortar, preferably made of agate to minimize contamination from the material of the mill during grinding, to form a powder the particle size of which is below 2 microns, i.e. the smallest wavelength in the mid-infrared range. Such a particle size can be achieved within a few minutes using a small grinding mill—e.g. a Wig-L-Bug microniser manufactured by Crescent Dental Manufacturing Company of the USA.

The powdered sample is placed in a diffuse reflectance cell, and the spectrum collected by an infrared spectrometer, preferably a Fourier transform infrared spectrometer. The equivalent transmission spectrum can be obtained by performing the Kubelka-Munk transform on the raw reflective spectrum data. This transform is described for example in the book Reference Spectroscopy by G. Kortoem, a Springer-Verlag publication, 1969. Such a transform is convenient only but not essential for the quantification; the diffuse reflectance spectrum corresponds to infrared radiation emitted by the solids molecules following their absorption of the radiation emitted by the infrared source of the spectrometer.

An alternative and better-known technique to collect the infrared spectrum of the mud solids is by direct transmission. The mixture of mud solids and halide salt is pressed into a solid disc (pellet) using a press capable of exerting loads of up to 10 tonnes. However, for the quantification of mud solids the diffuse reflectance technique is preferred for the reason given hereinbefore.

The diffuse reflectance spectrum of the recovered mud solids can be interpreted quantitatively using a number of techniques, including the Beer-Lambert law. In accordance with this law, there is a linear relationship between the diffuse reflectance—or the absorbance—of a product and its concentration at a single, fixed frequency, and the spectrum of a mixture can be analysed in terms of characteristic value of frequency for each of its individual components. However, a multivariate statistical technique, which uses the absorbance at a number of wavelengths, is preferred since a mixture of several components often results in marked deviations in the Beer-Lambert law. The spectrum of a mixture can be considered to be a linear combination of those of the pure components, and calibrations must be developed from the spectra of such mixtures. Multivariate statistical techniques can be used to generate a calibration model of the dried mud solids; the model essentially consists of a regression (or partial regression) of the spectral and concentration data sets of standards of accurately known compositions. Examples of such multivariate techniques are multiple linear regression, principal components analysis, and partial least squares path modelling. This last technique is preferred, and is described in the book *Multivariate Calibration* by H. Martens and T. Naes, a Wiley publication, 1989. An example of a computer programme to perform the partial least squares regression is the well-known UNSCRAMBLER software, developed at the Norwegian Food Research Institute and described in the journal *Chemometrics and Intelligent Laboratory Systems*, Volume 2, pages 239-243, 1987.

EXAMPLE 1

Quantification of the Various Components in Removed Solids and a Water-based Mud

DRILLING MUD

A typical weighted mud formulation containing bentonite, low viscosity carboxymethyl cellulose (CMC-LV), xanthan gum (XC) and barite was used to drill through formations of dolomitic limestone and gypsum. Average concentrations of each of the four mud products in the mud formulation are given below:

| | |
|---|---|
| Bentonite | 36 g/l |
| CMC-LV | 10 g/l |
| XC | 1 g/l |
| Barite | 180 g/l |

Drilled cuttings/solids generated by the solids control equipment contain each of the four mud product components, as well as four formation mineral components—dolomite, calcite, gypsum and quartz.

CALIBRATION

In order to quantify each of the mud products and formation minerals in samples of the drilled cuttings/solids generated during drilling, a quantitative calibration model was constructed using duplicate spectra for each of 21 calibration standards. Each standard was prepared by thoroughly mixing known weights of each pure component such that the weight fraction of each component varied within the ranges listed below:

| | | |
|---|---|---|
| Bentonite | 0.0079–0.0684 | |
| CMC-LV | 0.0011–0.0119 | |
| XC | 0.0005–0.0032 | Mud Products |
| Barite | 0.0634–0.1845 | |
| Dolomite | 0.0040–0.8589 | |
| Calcite | 0.0071–0.0367 | |
| Gypsum | 0.0077–0.7331 | Formation Minerals |
| Quartz | 0.0065–0.5560 | |

Whilst the composition of the calibration standards is dominated by a weight fraction of mineral components between 0.7835 and 0.9342, the weight fractions of mud product components constitute between 0.0658 and 0.2165 of the total composition. The xanthan gum (XC) component, originally present within a concentration range of 0.8–4.2 g/l in the original mud formation, constitutes a low weight fraction range of 0.0005–0.0032 in the calibration standards.

A total weight of two grams of each calibration standard was prepared; duplicate sub-samples of 0.45 grams were used to obtain a total of 42 FTIR spectra for the 21 calibration standards. Correlation coefficients for the calibration model generated from each of the 42 spectra are listed below:

| Component | Calibration coefficient | Comment |
|---|---|---|
| Bentonite | 0.972 | acceptable |
| CMC-LV | 0.977 | acceptable |
| XC | 0.993 | acceptable |
| Barite | 0.990 | acceptable |
| Dolomite | 0.999 | excellent (maximum) |
| Calcite | 0.991 | acceptable |
| Gypsum | 0.999 | excellent (maximum) |
| Quartz | 0.999 | excellent (maximum) |

Whilst the calibration correlation coefficients for the quantifications of the major minerals (dolomite, gypsum and quartz) are at a maximum, the corresponding coefficients for the minor mineral component (calcite) and the mud product components (bentonite, CMC-LV, XC and barite), are well above acceptable limits for their accurate quantification. FIGS. 2a, 2b and 2c show FTIR spectra for three calibration standards dominated by dolomite (FIG. 2a), gypsum and barite (FIG. 2b) and gypsum and quartz (FIG. 2c). Absorbance peaks due to fundamental vibrations of dolomite (v(u/4) at 730 cm$^{-1}$ and v(u/2) at 878 cm$^{-1}$) agree well with published values. Characteristic overtone peaks due to the dolomite component (at 2537, 2629, 2896 and 3023$^{-1}$) are well developed in this diffuse reflectance spectrum; such overtones are weakly developed in transmission spectra for the same calibration standard. Strongly developed overtone peaks in diffuse reflectance spectra for multicomponent mixtures may be essential for the quantification of trace components.

FIGS. 3a, 3b, 3c and 3d show the calibration curves used to quantify the mud product components (bentonite, CMC-LC, XC and barite, respectively). Corresponding curves used for the quantification of dolomite, calcite, gypsum and quartz are shown in FIGS. 4a, 4b, 4c and 4d.

TEST RESULTS

Results for a series of six test drilled cuttings/solids samples are given in Table 3. The samples (1 to 6) represent drilled cuttings samples generated by drilling across a lithological boundary between an upper dolomitic limestone (containing dolomite with some quartz) and a lower gypsum deposit (containing gypsum and quartz).

The four mud product components (bentonite, CMC-LV, XC and barite) are quantified in the test samples within average relative accuracies of ±10%, ±13%, ±30% and ±4% respectively. The relatively low accuracy of predicting XC concentrations in the test samples is attributed to a low absolute XC concentration range which may be nearing the lower limits for spectral deconvolution. However, the accuracy of predicting bentonite, CMC-LV and barite concentrations in the test samples is sufficient to justify a routine analysis of cuttings/solids removed by the solids control equipment in order that the three mud products are regularly accurately accounted for during the mud engineering service.

The four mineral components (dolomite, calcite, gypsum and quartz) are quantified in the test samples within average relative accuracies of ±3%, ±11%, ±12% and ±7% respectively. The relationship between relative accuracy for prediction of gypsum concentration and absolute gypsum concentration is shown in FIG. 5; clearly, the relative inaccuracy of predicting a gypsum concentration below approximately 3% must be taken into account when using such analyses to determine the efficiency of removing drilled solids generated at the interface between the upper dolomitic limestone and the lower gypsum deposit.

EXAMPLE 2

Quantification of the Various Components in Removed Solids and a Water-based Mud Containing Diesel Oil

DRILLING MUD

A typical weighted mud formulation containing bentonite, polyanionic cellulose (PAC), ferrochrome lignosulphonate (FCL), lignite, an asphaltene product, barite and diesel oil was used to drill through an upper formation "A" (containing calcite, quartz, and kaolinite) and a lower formation "B" (containing dolomite and anhydrite). Average concentrations of each of the seven mud products in the mud formulation are given below:

| | |
|---|---|
| Bentonite | 50 g/l |
| PAC | 5 g/l |
| FCL | 15 g/l |
| Lignite | 15 g/l |
| Asphaltene | 15 g/l |
| Barite | 180 g/l |
| Diesel oil | 50 ml/l |

CALIBRATION

In order to evaluate both the mud product and mineral components in return mud samples, a quantitative calibration model was constructed using duplicate spectra for each of 22 calibration standards. Each calibration mixture contains each mud product and mineral component varying in the weight fraction ranges listed below.

| | | |
|---|---|---|
| Bentonite | 0–0.1428 | |
| PAC | 0–0.0228 | |
| FCL | 0–0.0584 | |
| Lignite | 0–0.0492 | Mud Products |
| Asphaltene | 0–0.0514 | |
| Barite | 0–0.5242 | |
| Diesel oil | 0–0.0176 | |
| Calcite | 0–0.0246 | |
| Quartz | 0–0.0897 | |
| Kaolinite | 0–0.2050 | Formation Minerals |
| Dolomite | 0–0.5000 | |
| Anhydrite | 0–0.5000 | |

Duplicate sub-samples of each calibration standard were used to obtain a total of 44 FTIR spectra; calibration coefficients for the 12 components calibration model are listed below:

| Component | Calibration coefficient | Comment |
|---|---|---|
| Bentonite | 0.957 | acceptable |
| PAC | 0.991 | acceptable |
| FCL | 0.994 | acceptable |
| Lignite | 0.998 | acceptable |
| Asphaltene | 0.993 | acceptable |
| Barite | 0.992 | acceptable |
| Diesel oil | 0.993 | acceptable |
| Calcite | 0.935 | acceptable |
| Quartz | 0.998 | acceptable |
| Kaolinite | 0.998 | acceptable |
| Dolomite | 0.999 | excellent (maximum) |
| Anhydrite | 0.999 | excellent (maximum) |

Calibration coefficients for all twelve components are well above acceptable limits for their quantification. For example, FIGS. 6a, 6b, 6c and 6d show the calibration curves used to quantify PAC, FCL, Asphaltene and Diesel oil; corresponding curves for calcite, quartz and kaolinite are shown in FIGS. 7a, 7b and 7c.

Figure 6A:
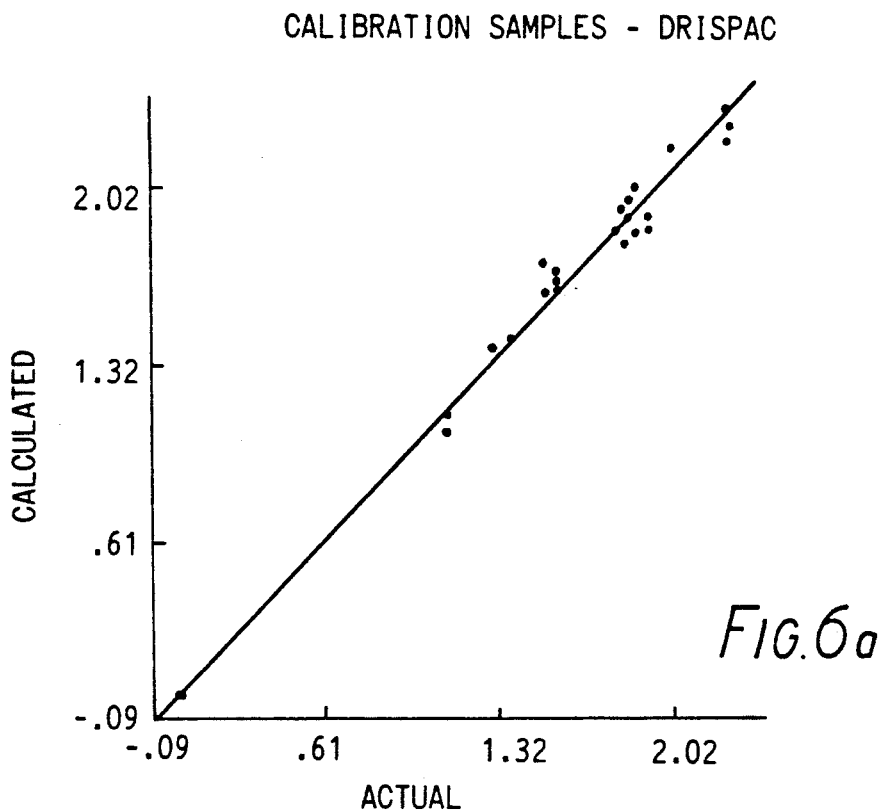
Figure 6B:
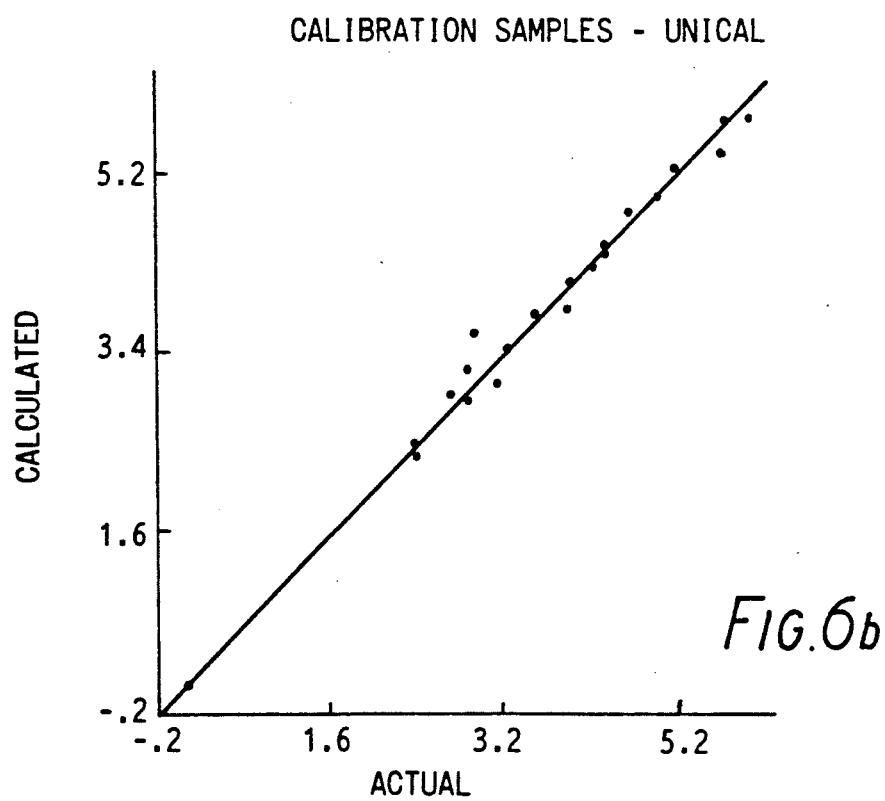
Figure 6C:
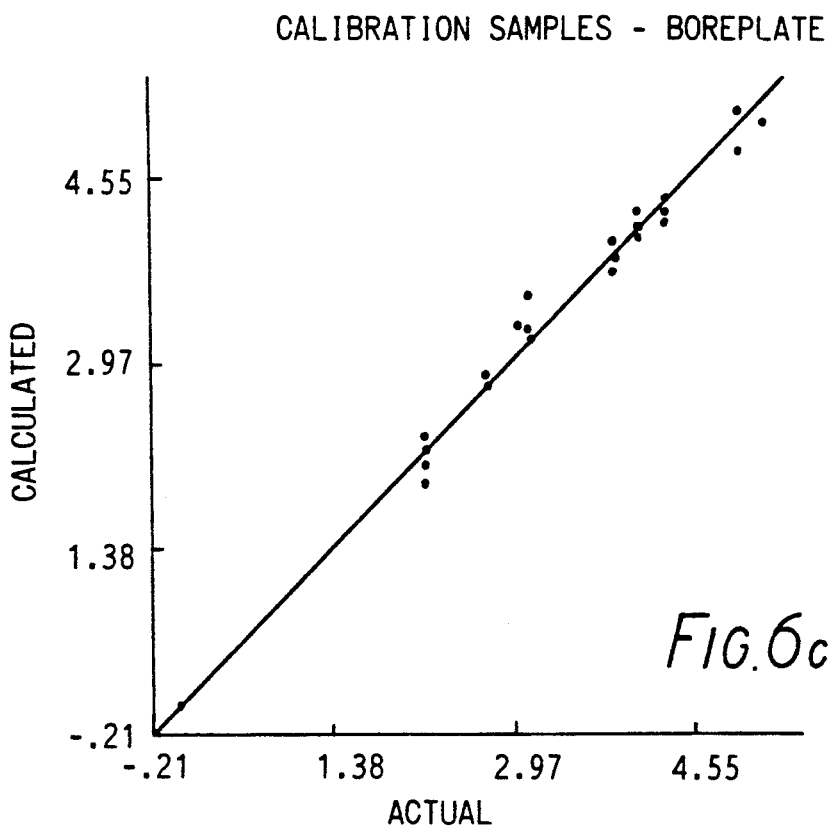
Figure 6D:
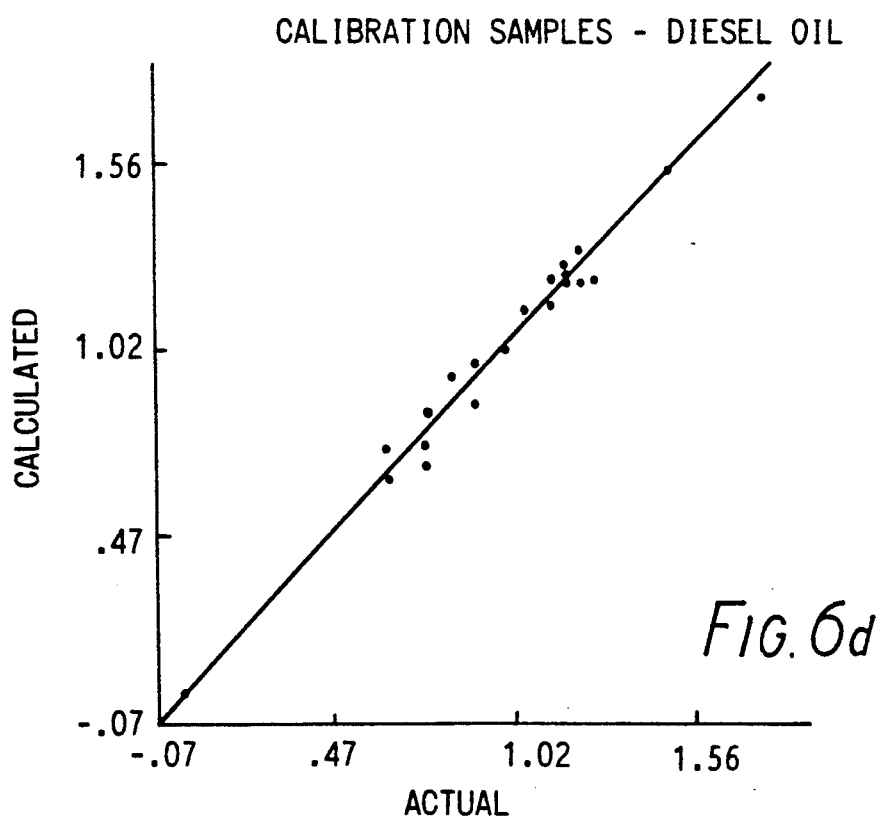

The quantification of diesel oil in a return mud and/or drilled cuttings/solid sample deserves special note. Sample preparation involves drying to constant weight so as to determine the weight fraction of solids, $W_{(S)}$. A drying temperature of 160° C. may be used to keep drying time to a minimum. At such a drying temperature, a large fraction of the diesel oil is volatile. However, the volatile fraction of a particular diesel oil will be a constant for a set drying temperature. Therefore, the concentration variance for diesel oil in calibration standards will be maintained through such a drying stage. FTIR spectra will show absorbance peaks due to the non-volatile friction; such spectral information is well correlated with concentration variance for a set of calibration standards as shown in FIG. 6d. The determination of diesel oil in an unknown sample involves a measurement using the calibration curve and a correction for the volatile fraction.

TEST RESULTS

Results for a series of three test return mud samples are given in Table 4. Test mud samples 1 and 2 contain drilled material originating from the upper formation "A", whilst test mud sample 3 also contains drilled material from formation "B". Over 80% of the data lies within a relative accuracy of ±10%. Drilled minerals are satisfactorily quantified together with a simultaneous analysis of the seven mud components.

TABLE 1

Mass balances designed to assess various aspects of a mud engineering service

| Mass Balance | Objective(s) | Input(s) Sample Name | Sampling Point | Output(s) Sample Name | Sampling Point |
|---|---|---|---|---|---|
| A | Assess drilled solids removal efficiency and mud products removed by shale shaker | Return mud | 38 | Drilled cuttings Shaker underflow | 40 44 |
| B | Assess drilled solids removal efficiency and mud products removed by solids control equipment | Shaker underflow | 44 | Drilled solids Solids control underflow | 42 46 46 |
| C (A & B) | Assess drilled solids removal efficiency and mud products removed by shale shaker and solids control equipment | Return mud | 38 | Drilled cuttings Drilled solids Solids control underflow | 40 42 46 |
| D | Assess hole stability for a drilled interval based on an indication of hole gauge. Assess mud product-formation component interactions | Suction mud | 16 | Return mud | 38 |
| E | Assess mixing properties of active tank | Solids control underflow Added "make-up" mud Addd mud products | 46 10 10 | Suction mud | 16 |

TABLE 2

Typical shale shaker mass balance
Mud formulation containing 36 g/l Bentonite, 10 g/l CMC-LV, 1 g/l XC and 208 g/l Barite used to drill a formation composed of 62.3% Dolomite, 2.2% Calcite, 20.5% Gypsum and 14.9% Quartz; [A] = 0.502 kg/s; [B] = 0.0209 (refer to equations (1) and (2)); data refers to 0.6 m³ of return mud input.

| Evaluated Stream | Total Volume (m³) | Total Mass (kg) | Density (kg/dm³) | Weight Fraction Solids $W_{(s)}$ | Mass Solids (kg) | Bentonite wt. % dry solids | Bentonite Mass (kg) | CMC-LV wt. % dry solids | CMC-LV Mass (kg) | XC wt. % dry solids | XC Mass (kg) | Barite wt. % dry solids | Barite Mass (kg) |
|---|---|---|---|---|---|---|---|---|---|---|---|---|---|
| INPUT | | | | | | | | | | | | | |
| Return mud | 0.6000 | 7200 | 1.2000 | 0.2333 | 1679.8 | 12.85 | 215.9 | 3.57 | 60.0 | 0.36 | 6.0 | 74.26 | 1247.4 |
| OUTPUT | | | | | | | | | | | | | |
| Drilled cuttings/ solids | 0.0093 | 159.75 | 1.7177 | 0.6666 | 106.5 | 1.95 | 2.1 | 0.54 | 0.6 | 0.06 | 0.06 | 11.31 | 12.0 |
| Shaker underflow mud | 0.5907 | 7040.25 | 1.1918 | 0.2235 | 1573.3 | 13.59 | 213.8 | 3.78 | 59.4 | 0.38 | 5.94 | 78.52 | 1235.4 |
| DRILLED SOLIDS REMOVAL EFFICIENCY (% OF INPUT) | | | | | | | | | | | | | |
| LOSS OF MUD COMPONENTS (% OF INPUT) | | | | | | | 1.0 | | 1.0 | | 1.0 | | 1.0 |

| | Evaluated Mineral Components | | | |
|---|---|---|---|---|
| | Dolomite | Calcite | Gypsum | Quartz |
| Weight | 0.6231 | 0.0221 | 0.2063 | 0.1485 |

TABLE 2-continued

Typical shale shaker mass balance
Mud formulation containing 36 g/l Bentonite, 10 g/l CMC-LV, 1 g/l XC and 208 g/l Barite used to drill a formation composed of 62.3% Dolomite, 2.2% Calcite, 20.5% Gypsum and 14.9% Quartz; [A] = 0.502 kg/s; [B] = 0.0209 (refer to equations (1) and (2)); data refers to 0.6 m³ of return mud input.

| Evaluated Stream | Total Volume (m³) | Total Mass (kg) | Density (kg/dm³) | Fraction Solids $W_{(s)}$ | Mass Solids (kg) | wt. % dry solids | Mass (kg) | wt. % dry solids | Mass (kg) | wt. % dry solids | Mass (kg) | wt. % dry solids | Mass (kg) |
|---|---|---|---|---|---|---|---|---|---|---|---|---|---|
| INPUT | | | | | | | | | | | | | |
| Return mud | 0.6000 | 7200 | 1.2000 | 0.2333 | 1679.8 | 5.58 | 93.7 | 0.20 | 3.3 | 1.85 | 31.0 | 1.33 | 22.3 |
| OUTPUT | | | | | | | | | | | | | |
| Drilled cuttings/solids | 0.0093 | 159.75 | 1.7177 | 0.6666 | 106.5 | 56.71 | 60.4 | 1.03 | 1.1 | 12.86 | 13.7 | 15.49 | 16.5 |
| Shaker underflow mud | 0.5907 | 7040.25 | 1.1918 | 0.2235 | 1573.3 | 2.12 | 33.3 | 0.14 | 2.2 | 1.10 | 17.3 | 0.37 | 5.8 |
| DRILLED SOLIDS REMOVAL EFFICIENCY (% OF INPUT) | | | | | | 64.5 | | 33.3 | | 44.2 | | 74.0 | |
| LOSS OF MUD COMPONENTS (% OF INPUT) | | | | | | | | | | | | | |

TABLE 3

Results for six test drilled cuttings/solids calculated using calibration model (Example 1)

| | TEST MUD BATCH NUMBER | | | | | |
|---|---|---|---|---|---|---|
| | 1 | 2 | 3 | 4 | 5 | 6 |
| QUANTIFICATION OF MUD COMPONENTS wt. % dry solids | | | | | | |
| BENTONITE | | | | | | |
| Actual | 4.70 | 2.70 | 3.75 | 1.62 | 2.26 | 2.42 |
| Measured | 3.80 | 2.13 | 3.27 | 1.57 | 2.33 | 2.31 |
| *Difference | −0.90 | −0.57 | −0.48 | −0.05 | +0.07 | −0.11 |
| Relative Diff | −19 | −21 | −12 | −3 | +3 | −4.5 |
| CMC-LV | | | | | | |
| Actual | 0.60 | 0.76 | 0.77 | 0.37 | 0.63 | 0.38 |
| Measured | 0.85 | 0.75 | 0.71 | 0.44 | 0.66 | 0.39 |
| Difference | +0.25 | −0.01 | −0.06 | +0.07 | +0.03 | +0.01 |
| Relative Diff | +42 | −1 | −8 | +19 | +5 | +3 |
| XC | | | | | | |
| Actual | 0.19 | 0.13 | 0.13 | 0.21 | 0.06 | 0.26 |
| Measured | 0.25 | 0.18 | 0.17 | 0.13 | 0.04 | 0.28 |
| Difference | +0.06 | +0.05 | +0.04 | −0.08 | −0.02 | +0.02 |
| Relative Diff | +32 | +38 | +30 | −38 | −33 | +8 |
| BARITE | | | | | | |
| Actual | 12.30 | 11.37 | 6.34 | 11.87 | 11.80 | 7.86 |
| Measured | 12.50 | 10.16 | 6.96 | 11.89 | 11.81 | 7.57 |
| Difference | +0.20 | +1.21 | +0.62 | +0.02 | +0.01 | −0.29 |
| Relative Diff | +1.6 | −11 | +10 | +0.2 | 0 | −4 |
| QUANTIFICATION OF MINERAL COMPONENTS wt. % dry solids | | | | | | |
| DOLOMITE | | | | | | |
| Actual | 71.95 | 56.39 | 59.74 | 59.62 | 53.12 | 16.15 |
| Measured | 70.95 | 58.38 | 57.37 | 59.21 | 53.89 | 17.40 |
| Difference | −1.00 | +1.99 | −2.39 | −0.41 | +0.77 | +1.25 |
| Relative Diff | −1.4 | +3.5 | −4 | −0.7 | +1.4 | +8 |
| CALCITE | | | | | | |
| Actual | 2.15 | 1.95 | 2.09 | 1.67 | 1.88 | 1.77 |
| Measured | 2.48 | 1.94 | 1.83 | 1.42 | 1.45 | 1.75 |
| Difference | +0.33 | −0.01 | −0.26 | −0.25 | −0.43 | −0.02 |
| Relative Diff | +15 | −0.5 | −12 | −15 | −23 | −1 |
| GYPSUM | | | | | | |
| Actual | 0.77 | 4.11 | 5.36 | 9.94 | 17.59 | 34.92 |
| Measured | 0.40 | 3.81 | 4.67 | 9.79 | 18.11 | 34.94 |
| Difference | −0.37 | −0.3 | −0.69 | −0.15 | +0.52 | +0.02 |
| Relative Diff | −48 | −7 | −13 | −1.5 | +3 | 0 |
| QUARTZ | | | | | | |
| Actual | 3.41 | 22.62 | 21.81 | 14.70 | 12.66 | 36.23 |
| Measured | 2.77 | 22.14 | 23.48 | 13.75 | 11.79 | 36.18 |
| Difference | −0.64 | −0.48 | +1.67 | −0.95 | −0.87 | −0.05 |

TABLE 3-continued

Results for six test drilled cuttings/solids calculated using calibration model (Example 1)

| | TEST MUD BATCH NUMBER | | | | | |
|---|---|---|---|---|---|---|
| | 1 | 2 | 3 | 4 | 5 | 6 |
| Relative Diff | −19 | −2 | +8 | −6 | −7 | 9 |

*Difference = Measured − Actual
Relative Diff = [Measured − Actual]/Actual. 100%

TABLE 4

Results for three test return muds calculated using calibration model (Example 2)

| | TEST MUD BATCH NUMBER | | |
|---|---|---|---|
| | 1 | 2 | 3 |
| QUANTIFICATION OF MUD COMPONENTS wt. % dry solids | | | |
| Bentonite | | | |
| Actual | 11.52 | 10.93 | 11.26 |
| Measured | 11.65 | 11.25 | 11.35 |
| *Difference | +0.13 | +0.32 | +0.09 |
| Relative Diff | +1.1 | +3 | 0.8 |
| PAC | | | |
| Actual | 1.18 | 1.35 | 1.16 |
| Measured | 1.30 | 1.42 | 1.34 |
| Difference | +0.12 | +0.07 | +0.18 |
| Relative Diff | +10 | +5 | +16 |
| FCL | | | |
| Actual | 4.61 | 4.37 | 4.50 |
| Measured | 5.10 | 5.30 | 4.81 |
| Difference | +0.49 | +0.93 | +0.31 |
| Relative Diff | +11 | +21 | +7 |
| Lignite | | | |
| Actual | 3.46 | 4.13 | 3.38 |
| Measured | 3.95 | 3.95 | 3.14 |
| Difference | +0.49 | −0.18 | −0.24 |
| Relative Diff | +14 | −4 | −7 |
| Asphaltene | | | |
| Actual | 3.50 | 3.40 | 3.42 |
| Measured | 3.38 | 3.16 | 3.44 |
| Difference | −0.12 | −0.24 | +0.02 |
| Relative Diff | −3 | −7 | +0.6 |
| Barite | | | |
| Actual | 45.87 | 44.99 | 44.83 |
| Measured | 44.10 | 43.70 | 43.30 |
| Difference | −1.77 | −1.29 | −1.53 |
| Relative Diff | −4 | −3 | −3 |
| Diesel Oil | | | |
| Actual | 1.07 | 1.24 | 1.05 |
| Measured | 1.13 | 1.32 | 1.14 |
| Difference | +0.06 | +0.08 | +0.09 |
| Relative Diff | +6 | +6 | +9 |
| QUANTIFICATION OF MINERAL COMPONENTS wt. % dry solids | | | |
| Calcite | | | |
| Actual | 1.24 | 1.94 | 1.21 |
| Measured | 1.31 | 1.37 | 1.40 |
| *Difference | +0.07 | −0.57 | +0.19 |
| Relative Diff | +6 | −30 | +16 |
| Quartz | | | |
| Actual | 6.91 | 8.36 | 6.76 |
| Measured | 6.50 | 7.85 | 7.20 |
| Difference | −0.41 | −0.51 | +0.44 |
| Relative Diff | −6 | −6 | +7 |
| Kaolinite | | | |
| Actual | 13.60 | 11.90 | 13.29 |
| Measured | 13.55 | 13.40 | 16.90 |
| Difference | −0.05 | +1.50 | +3.61 |
| Relative Diff | 0 | +13 | +27 |
| Dolomite | | | |
| Actual | 0 | 0 | 0.80 |
| Measured | 0 | 0 | 0.90 |
| Difference | — | — | +0.10 |
| Relative Diff | — | — | +13 |
| Anhydrite | | | |
| Actual | 0 | 0 | 10.01 |
| measured | 0 | 0 | 12.00 |
| Difference | — | — | +1.99 |
| Relative Diff | — | — | +20 |

*Difference = Measured − Actual
Relative Diff = [Measured − Actual]/Actual. 100%

We claim:

1. A method of quantitative analysis of drilled cuttings/solids samples obtained in the course of the drilling of a borehole using a drilling fluid, in which method the solids removed by one or more of the solids control devices are representatively sampled and the sample is analysed, the method comprising the following steps:
   the sample is homogenised;
   a known weight of the homogenised sampled is dried to constant weight, and the weight fraction of solids $W_{(S)}$, in the sample is determined;
   the dried solids are crushed and homogenised to form a powder suitable for quantitative infrared analysis, and the powder is analysed in a IR spectrometer in order to obtain an infrared spectrum; and
   knowing the solids weight fraction, a value representative of the quantity of at least one of the mud product components and/or at least one of the mineral components in the sample is determined from the spectrum.

2. The method of claim 1, wherein the infrared spectrum is obtained by a diffuse reflectance technique.

3. The method of claim 2, wherein the transmission spectrum equivalent to the diffuse reflectance spectrum is obtained by performing a Kubelka-Munk transform on the diffuse reflectance spectrum.

4. The method of claim 1, further comprising the steps of determining the weight of salt $M_e$ dissolved in a known weight of removed solids and correcting the weight fraction of solids $W_s$ in the removed solids to account for $M_e$.

5. The method of claim 1, wherein the removed solids samples are homogenised in a high speed blender, and then dried to constant weight using an infrared drier balance.

6. The method of claim 1, wherein the dried solids powdered for infrared analysis are so powdered without any additives thereto or carriers therefor.

7. The method of claim 1, wherein the step of preparing the dried solids to form a powder comprises mixing a known weight of dried solids with a halide salt to form a mixture and grinding the mixture until the particle size of the solids is no more than 2 microns to obtain said powder.

8. The method of claim 7 wherein the halide salt is potassium bromide or sodium chloride.

9. The method of claim 1, wherein the step of determining a value representative of the quantity of at least one of the products from the infrared spectrum comprises obtaining infrared spectra of standards containing known concentrations of said drilling fluid products, and generating a calibrations model from said infrared spectra.

10. The method of claim 1, wherein the density $\rho_{(s)}$ of the homogenised sample is determined, and thereafter the concentration of the selected component is determined from the infrared spectrum.

11. The method of claim 1, wherein the infrared spectrum obtained by analysing the powder is a Fourier transform infrared spectrum.

12. The method of claim 1, wherein said at least one of the components is selected from the group consisting of polymer, drilled clay, bentonite clay, barite, oils, carbonates, quartz, felspar, clay minerals and sulphates.

13. The method of claim 1, in which a given concentration of one of the products is indicated in the drilling fluid specifications, further comprising the steps of comprising said given concentration with the determined concentration of said product, and adjusting the determined concentration of said product so as to comply with the drilling fluid specifications.

14. The method of claim 1, wherein the working condition of the mud solids equipment is assessed by monitoring the variation in the quantity of one of the products treated by the mud solids equipment.

15. The method of claim 14, wherein the working condition of the mud solids equipment is assessed upstream and downstream of said mud solids equipment.

16. The method of claim 1 further comprising the step of controlling the drilling operation according to data obtained from monitoring the presence and concentration of products present in the removed solids and coming from the formation being drilled and/or the borehole wall.

* * * * *